United States Patent [19]

Connor et al.

[11] 4,127,669

[45] Nov. 28, 1978

[54] [(4-OXO-4H-1-BENZOPYRAN-3-YL)OXY] ACETIC ACIDS AND DERIVATIVES

[75] Inventors: David T. Connor, Ann Arbor, Mich.; Patricia A. Young, Madison, N.J.; Maximillian von Strandtmann, New Castle, Del.

[73] Assignee: Warner-Lambert Company, Morris Plains, N.J.

[21] Appl. No.: 841,781

[22] Filed: Oct. 13, 1977

[51] Int. Cl.² .................. A61K 31/35; C07D 311/76; C07D 257/04; A61K 31/41
[52] U.S. Cl. ................................ 424/283; 260/345.2; 260/345.5; 260/308 D; 424/269
[58] Field of Search .................. 260/345.2, 345.5; 424/283

[56] References Cited

U.S. PATENT DOCUMENTS 3,849,446  11/1974  Strandtmann et al. ........... 260/345.2

Primary Examiner—Nicky Chan
Attorney, Agent, or Firm—Albert H. Graddis; Frank S. Chow; Anne M. Kelly

[57] ABSTRACT

Compounds of formula I:

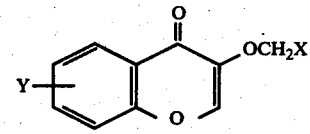

wherein Y is hydrogen, lower alkyl, halogen or lower alkoxy; X is carboxy, alkoxycarbonyl, carboxamide, cyano or tetrazolo, and their non-toxic, pharmaceutically acceptable salts are disclosed. These compounds are useful in the prevention of allergic and asthmatic reactions.

10 Claims, No Drawings

[(4-OXO-4H-1-BENZOPYRAN-3-YL)OXY] ACETIC ACIDS AND DERIVATIVES

This invention relates to compounds of formula I:

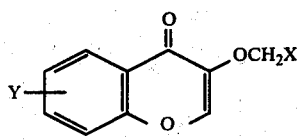

wherein Y is hydrogen, lower alkyl, halogen or lower alkoxy; X is carboxy, alkoxycarbonyl, carboxamide, cyano or tetrazolo.

Also embraced within the scope of this invention are the non-toxic, pharmaceutically acceptable salts of the compounds of formula I such as the sodium salt, the calcium salt and the like. Especially preferred are those compounds of the formula I wherein Y is hydrogen or lower alkoxy.

The compounds of the formula I are prepared by the route shown in reaction Scheme A from 3-hydroxychromones:

SCHEME A

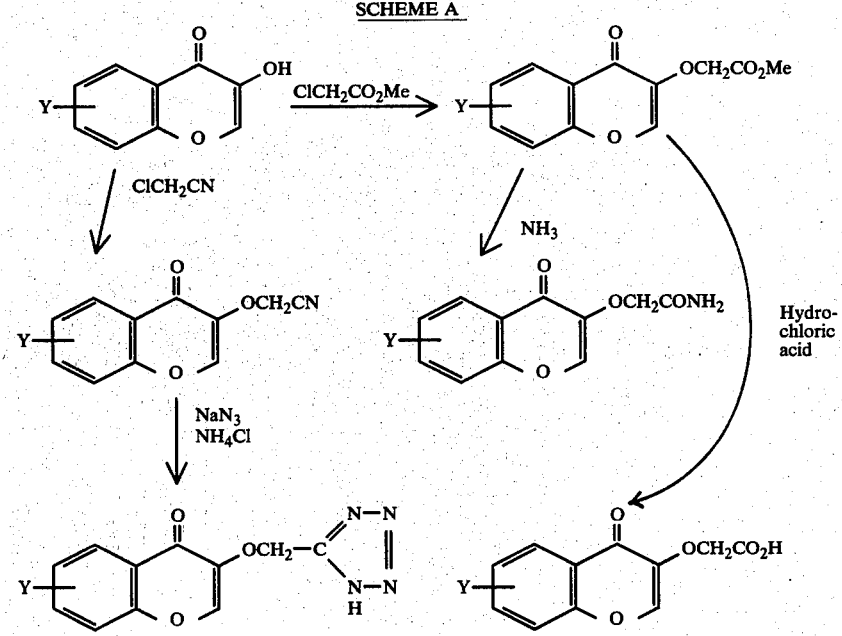

The starting 3-hydroxychromones were prepared by the method of F. Arndt and B. Eistert, *Chem. Berichte*, 62:36 (1929) wherein chromanone (unsubstituted or substituted by lower alkyl, halogen or lower alkoxy on the aromatic ring) is reacted with amyl nitrite to obtain the correspondingly substituted 3-nitroso chromanone which may then be hydrolyzed to obtain the desired 3-hydroxychromone starting material.

The starting 3-hydroxychromones may also be prepared according to the reaction Scheme B from 3-(methylsulfinyl) chromanones:

SCHEME B

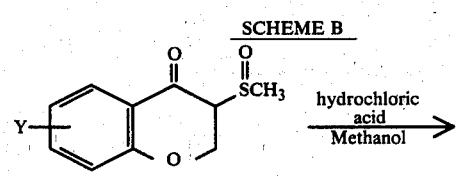

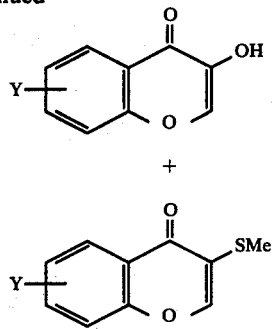

In aforementioned Scheme B, the 3-(methylsulfinyl)-chromanones are prepared according to a general process described by M. von Strandtmann, et al., in *J. Heterocyclic Chem.* 9:171 (1972) whereby a salicyclic ester (which may be unsubstituted or substituted by lower alkyl, halogen, lower alkoxy) is treated with sodium methylsulfinyl carbanion generated by the action of sodium hydride on dimethylsulfoxide to obtain a correspondingly substituted ortho-hydroxy-ω-(methylsulfinyl)acetophenone which is then cyclized by reaction with 1 mole of formaldehyde to obtain the desired 3-(methylsulfinyl)chromanone.

The compounds of this invention having the formula I are active in the prevention of allergic conditions (typically, asthmatic reactions) in mammals such as rats as evidenced by positive results in the passive cutaneous anaphylaxis screen (PCA Test). The PCA screen is a modification of the procedure described by I. Mota, *Life Sciences*, Vol. 4, No. 7:465-474 (1963) and Z. Ovary and O. Bier, *Proc. Soc. Exptl. Biol. Med.*, 81:584-586 (1952) and provides a measure of the effectiveness of test compounds in inhibiting the release or action of toxic products arising from the combination of reaginic antibodies with specific antigens. These toxic products are causative factors in such disorders as bronchial allergic asthma (extrinsic reagins), exercise asthma, cold asthma, hay fever, perennial allergic rhinitis, food allergies, serum or drug allergies, insect sting allergies, angioneurotic edema, atopic dermatitis, including infantile excema, urticaria, dermographism, dermatoconjunctivitis, acute allergic conjunctivitis, chronic allergic conjunctivitis, and the like.

Inhibition of reaginic antigen/antibody reactions in experimental animals such as rats is regarded as representative of inhibition of human reaginic antigen/antibody reactions which occur during allergic episodes.

Thus, the compounds of this invention having the formula I are active for the inhibition of reagin-mediated allergic disorders in mammals in need thereof at dose levels of from about about 0.5 to about 100 mg/kg of body weight when administered parenterally or by pulmonary administration via the buccal cavity. Thus, for example, [(8-methoxy-4-oxo-4H-benzopyran-3-yl)-oxy]acetic acid (the compound of Example 3) shows a 20% inhibition of the allergic response at 0.5 mg/kg when administered intervenously to rats in the passive cutaneous anaphalaxis (PCA) screen. Accordingly, the compounds of this invention having the formula I are useful in the treatment of asthma, hay fever and other allergic conditions.

In use, the compounds of the invention having the formula I may be combined with parenterally acceptable vehicles, such as gum tragacanth, in saline suspension, to provide dosage forms suitable for parenteral administration.

For pulmonary administration, the compounds of the invention having the formula I in dry powder form may be formulated with non-toxic, pharmaceutically acceptable propellants known to the pharmacist's art or they may be dispensed in powder form from a powder inhalation device. Compositions in the form of dry powders preferably may include a solid fine powder diluent.

In all of the above formulas, and throughout the specification, the terms "lower alkyl" and "lower alkoxy" are meant to include lower aliphatic hydrocarbons having 1 to 7 carbon atoms (preferably 1 to 4 carbon atoms) in the carbon chain, such as methyl, ethyl, propyl, isopropyl, butyl or isobutyl; and the term "halogen" is meant to include bromine, chlorine, iodine and fluorine.

To further illustrate the practice of this invention, the following examples are included.

EXAMPLE 1

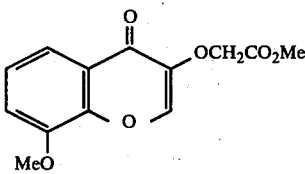

Methyl[(8-methoxy-4-oxo-4H-1-benzopyran-3-yl)oxy-]acetate

A mixture of 3-hydroxy-8-methoxychromone (1.92 g, 0.01 mole), methyl chloracetate (1.08 g, 0.01 mole) and potassium carbonate (1.0 g, 0.01 mole) in dimethylformamide (20 ml) is stirred at 100° C. under nitrogen for 4 hrs. The reaction mixture is allowed to stand at room temperature overnight, poured into water, filtered, washed with water and sucked dry. Recrystallization from ethanol gives white crystals (2.3 g, 88%), mp 137°-138° C.

Anal. Calcd, for $C_{13}H_{12}O_6$: C, 59.09; H, 4.58. Found: C, 59.04; H, 4.67.

EXAMPLE 2

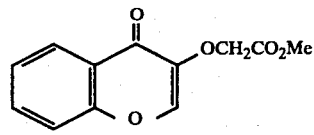

Methyl [(4-oxo-4H-1-benzopyran-3-yl)oxy]acetate

Prepared from 3-hydroxychromone (12 g, 0.074 mole) by the general method described in Example 1. Recrystallization from absolute ethanol gives light brown crystals (13.2 g, 83%), mp 114°-116° C.

Anal. Calcd. for $C_{12}H_{10}O_5$: C, 61.54; H, 4.30. Found: C, 61.57; H, 4.40.

EXAMPLE 3

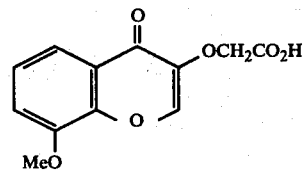

[(8-Methoxy-4-oxo-4H-1-benzopyran-3-yl)oxy]acetic acid

A suspension of methyl [(8-methoxy-4-oxo-4H-1-benzopyran-3-yl)oxy]acetate (200 mg) in 6N hydrochloric acid (20 ml) is stirred at 100° C. for 3 hrs. under nitrogen. The reaction is cooled and the product filtered off and sucked dry. Recrystallization from methanol gives white crystals (180 mg. 86%), mp 215°-217° C.

Anal. Calcd. for $C_{12}H_{10}O_6$: C, 57.60; H, 4.03. Found: C, 57.47; H, 4.24.

EXAMPLE 4

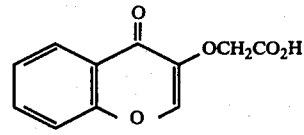

[(4-Oxo-4H-1-benzopyran-3-yl)oxy]acetic acid

Prepared from methyl [(4-oxo-4H-1-benzopyran-3-yl)oxy]acetate (7.3 g) by the general method described in Example 3. Recrystallization from absolute ethanol gives tan colored crystals (3.7 g, 54%), mp 154°-164° C.

Anal. Calcd. for $C_{11}H_8O_5$: C, 60.00; H, 3.66. Found: C, 59.84; H, 3.83.

EXAMPLE 5

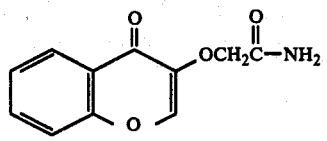

2-[(4-Oxo-4H-1-benzopyran-3-yl)oxy]acetamide

Ammonia is bubbled through a cooled (ice-bath) suspension of methyl [(4-oxo-4H-1-benzopyran-3-yl)oxy]acetate (2 g) in ethanol (100 ml) for 15 min. An homogeneous solution formed and is stirred at room temperature for 3 hrs. The solvents are removed at reduced pressure to give a brown gum, which crystallizes from methanol. Recrystallization from dimethylformamide gives white crystals (450 mg, 24%), mp 208°–210° C.

Anal. Calcd. for $C_{11}H_9NO_4$: C, 60.27; H, 4.14; N, 6.39. Found: C, 60.09; H, 4.18; N, 6.49.

EXAMPLE 6

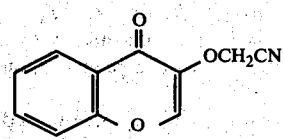

[(4-Oxo-4H-1-benzopyran-3-yl)oxy]acetonitrile

A mixture of 3-hydroxychromone (4.86 g, 0.03 mole), chloroacetonitrile (2.26 g, 0.03 mole) and potassium carbonate (3.0 g, 0.02 mole) in dimethylformamide (40 ml) is stirred at 100° C. under nitrogen for 4 hrs. The reaction mixture is cooled, poured into water (200 ml), filtered, washed with water and sucked dry. Recrystallization from methanol gives white crystals (4.7 g, 94%), mp 145°–146° C.

Anal. Calcd. for $C_{11}H_7NO_3$: C, 65.57; H, 3.51; N, 6.96. Found: C, 65.56; H, 3.54; N, 6.85.

EXAMPLE 7

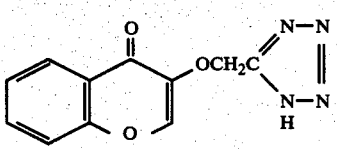

3-(1H-Tetrazol-5-ylmethoxy)-4H-1-benzopyran-4-one

A mixture of [(4-oxo-4H-1-benzopyran-3-yl)oxy]acetonitrile (2.0 g, 0.01 mole), sodium azide (0.715 g, 0.011 mole) and ammonium chloride (0.56 g, 0.012 mole) in DMF (10 ml) is heated at 125° C. for 7 hrs. under nitrogen. The reaction is cooled overnight and then poured into excess cold water. The aqueous is acidified with 5N hydrochloric acid and the insoluble product is filtered, washed with fresh water and sucked dry. Recrystallization from absolute ethanol gives beige colored crystals (1.45 g, 60%), mp 194°–196° C.

Anal. Calcd. for $C_{11}H_8N_4O_3$: C, 54.10; H, 3.30; N, 22.94. Found: C, 53.83; H, 3.34; N, 22.76.

EXAMPLE 8

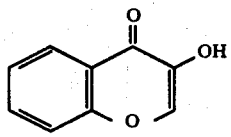

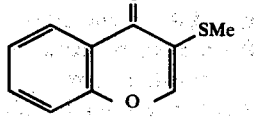

3-Hydroxychromone (1) and 3-(methylthio)chromone (2)

A mixture of 3-(methylsulfinyl)chromanone (11 g), methanol (100 ml) and 1N hydrochloric acid (100 ml) is stirred at room temperature for 20 hrs. The methanol is removed at reduced pressure, and the aqueous residue is extracted with chloroform. The chloroform extracts are combined, extracted with 1N sodium hydroxide solution, washed with water, dried over $MgSO_4$ and evaporated to give an oil. The oil is heated at 100° C. in 5N hydrochloric acid (100 ml) for 5 hrs. The solution is cooled, and the product which precipitated is filtered off. Recrystallization from methanol gives 3-(methylthio)chromone (2) as white crystals (7.2 g, 72%), mp 103°–105° C.

Anal. Calcd. for $C_{10}H_8O_2S$: C, 62.48; H, 4.20; S, 16.68. Found: C, 62.34; H, 4.26; S, 16.24.

The sodium hydroxide solution extracts are acidified with 5N hydrochloric acid and extracted with chloroform. The chloroform extracts are dried over $MgSO_4$ and evaporated to a solid product. Recrystallization from ethanol gives 3-hydroxychromone (1) as white crystals (2.1 g, 25%) mp 178°–179° C.

Anal. Calcd. for $C_9H_6O_3$: C, 66.67; H, 3.73. Found C, 66.27; H, 3.79.

EXAMPLE 9

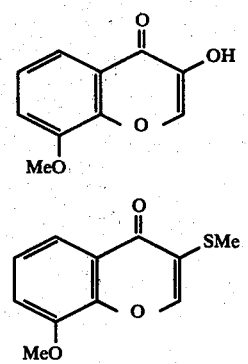

8-Methoxy-3-hydroxychromone (1) and 8-methoxy-3-(methylthio)chromone (2)

A mixture of 8-methoxy-3-(methylsulfinyl)chromanone (20 g), methanol (100 ml) and 1N hydrochloric acid (100 ml) is stirred at room temperature for 20 hrs. The methanol is removed at reduced pressure and the aqueous residue is extracted with chloroform. The chloroform extracts are combined, extracted with 1N sodium hydroxide solution, washed with water, dried over $MgSO_4$ and evaporated to give an oil. The oil is heated at 100° C. in 5N hydrochloric acid (100 ml) for 5 hrs. The solution is cooled and the product which precipitated is filtered off. Recrystallization from ethanol gives 8-methoxy-3-(methylthio)chromone (2) as white crystals (12.1 g, 65%), mp 113°–115° C.

Anal. Calcd. for $C_{11}H_{10}O_3S$: C, 59.44; H, 4.54; S, 14.43. Found: C, 59.23; H, 4.58; S, 14.48.

The sodium hydroxide solution extracts are acidified with 5N hydrochloric acid and extracted with chloroform. The chloroform extracts are dried over $MgSO_4$ and evaporated to give a yellow solid. Recrystallization from ethanol gives 8-methoxy-3-hydroxychromone (1) as yellow crystals (3.64 g, 23%), mp 180°–183° C.

Anal. Calcd. for $C_{10}H_8O_3$: C, 62.50; H, 4.20. Found: C, 62.77; H, 4.19.

We claim:

1. A compound of the formula I:

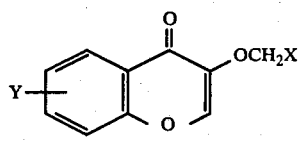

wherein Y is hydrogen, lower alkyl, halogen or lower alkoxy; X is carboxy, alkoxycarbonyl, carboxamide or cyano, and the non-toxic, pharmaceutically acceptable salts thereof.

2. The compound according to claim 1 wherein Y is hydrogen or lower alkoxy.

3. The compound according to claim 1 which is methyl [(8-methoxy-4-oxo-4H-1-benzopyran-3-yl)oxy]acetate.

4. The compound according to claim 1 which is methyl [(4-oxo-4H-1-benzopyran-3-yl)oxy]acetate.

5. The compound according to claim 1 which is [(8-methoxy-4-oxo-4H-1-benzopyran-3-yl)oxy]acetic acid.

6. The compound according to claim 1 which is [(4-oxo-4H-1-benzopyran-3-yl)oxy]acetic acid.

7. The compound according to claim 1 which is 2-[(4-oxo-4H-1-benzopyran-3-yl)oxy]acetamide.

8. The compound according to claim 1 which is [(4-oxo-4H-1-benzopyran-3-yl)oxy]acetonitrile.

9. A pharmaceutical composition for inhibiting reagin-mediated allergic manifestations in mammals in need thereof, which comprises an effective amount of a compound of the formula I:

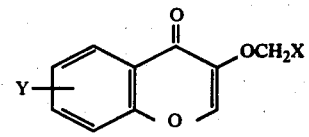

wherein Y is hydrogen, lower alkyl, halogen or lower alkoxy; X is carboxy, alkoxycarbonyl, carboxamide or cyano, and the non-toxic, pharmaceutically acceptable salts thereof together with a pharmaceutically acceptable carrier therefor.

10. A method for inhibiting reagin-mediated allergic manifestations in mammals in need thereof, which comprises the administration of an effective amount of a compound of the formula I:

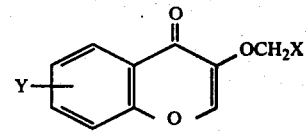

wherein Y is hydrogen, lower alkyl, halogen or lower alkoxy; X is carboxy, alkoxycarbonyl, carboxamide or cyano, and the non-toxic, pharmaceutically acceptable salts thereof.